United States Patent [19]

Bloczynski

[11] Patent Number: 5,631,371
[45] Date of Patent: May 20, 1997

[54] METHOD FOR THE PREPARATION OF SUBSTITUTED 3-(PHENYLIMINO)-3H-PHENOTHIAZINES AND PHENOXAZINES

[75] Inventor: Michael L. Bloczynski, Elkhart, Ind.

[73] Assignee: Bayer Corporation, Elkhart, Ind.

[21] Appl. No.: 562,164

[22] Filed: Nov. 22, 1995

[51] Int. Cl.$^6$ .................. C07D 279/18; C07D 265/38
[52] U.S. Cl. ........................... 544/37; 544/102
[58] Field of Search ........................ 544/102, 37

[56] References Cited

U.S. PATENT DOCUMENTS

| 4,125,717 | 11/1978 | Psaar ....................... 544/102 |
| 4,362,873 | 12/1982 | Belfort ...................... 544/103 |

OTHER PUBLICATIONS

Swern, Organic Peracids, Chem. Rev., 45, pp. 1–68, 1949.
House, Modern Synthetic Reactions, 2nd Edition, pp. 292–296 and 353–359, 1972.
Holmes et al., A simple method for the direct oxidation of aromatic amines to nitroso compounds, J. American Chemical Society, vol. 82, pp. 3454–3456, 1960.

*Primary Examiner*—Mukund J. Shah
*Assistant Examiner*—Deepak R. Rao
*Attorney, Agent, or Firm*—Jerome L. Jeffers

[57] ABSTRACT

The present invention involves a method for the preparation of substituted 3-(phenylimino)-3H-phenothiazines or phenoxazines which method involves reacting phenothiazine or phenoxazine with an aromatic amine in the presence of periodic acid as coupling agent.

10 Claims, No Drawings

METHOD FOR THE PREPARATION OF SUBSTITUTED 3-(PHENYLIMINO)-3H-PHENOTHIAZINES AND PHENOXAZINES

BACKGROUND OF THE INVENTION

In U.S. Pat. No. 4,710,570 there are disclosed 3-(phenylamino)-3H-phenoxizines or phenothiazines of the type whose preparation is the subject matter of the present invention. This patent discloses that these compounds have utility in, photothermographic imaging and more particularly that the "leuko" or reduced form of these dyes are suitable as dye-forming agents in pressure sensitive, thermographic, photothermographic and photographic imaging systems. The '570 patent discloses the preparation of these compounds by the oxidation of phenothiazine with iodine to form a phenothiazin-5-ium perhalide and the subsequent treatment with an amine to yield a 3-(substituted amino)-phenothiazin-5-ium salt. This method suffers from the disadvantage that it provides low yields and mixed products which require extensive purification.

In co-pending application, Ser. No. 471,745 there is disclosed the use of these compounds as mediators for the electrochemical regeneration of the coenzymes dihydronicotinamide adenine dinucleotide (NADH) and dihydronicotinamide adenine dinucleotide phosphate (NADPH). In this patent application, there is described the preparation of the 3-phenylimino phenoxizines and phenothiazines by the reaction of roughly equi-molar concentrations of the appropriate phenoxizine or phenothiazine with the appropriate aniline in the presence of 1 molar silver nitrate in methanol. This method of preparation is not fully satisfactory because it does not work well with all substituted aromatic amines and a silver precipitate must be removed from the product.

Baranov et al report the oxidative condensation of phenothiazine with aromatic amines using ferric chloride as the oxidative coupling agent in *Zhurnal Organicheskoi Khimti*, Vol. 27, No. 9, 2008 (1989).

In general, there are only a few literature methods for the preparation of substituted 3-phenylamino compounds and they suffer from low yields, the need for extensive purification and poor characterization of the resulting products. Since these compounds are only slightly soluble in organic solvents, large amounts of chloroform (a carcinogen) and costly silica gel are used for purification.

It is an object of the present invention to provide a novel process for the preparation of 3-(phenylamino)-3H-phenoxazines or phenothiazines which provides high yields while using inexpensive and environmentally safe reagents without extensive purification.

SUMMARY OF THE INVENTION

The present invention involves a method for the preparation of 3-(phenylamino)-3H-phenothiazines or phenoxizines of the formula:

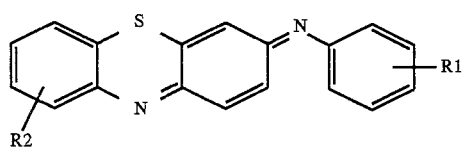

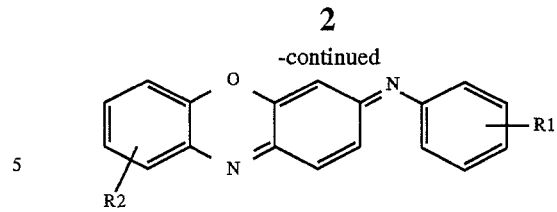

wherein R1 and R2 are H or one or more substituent which serve to moderate the reduction-oxidation potential of the compound, to vary the compound's solubility or to function as a site for the covalent attachment of the compound to a polymer or solid support which method comprises reacting a phenothiazine or phenoxazine of the formula:

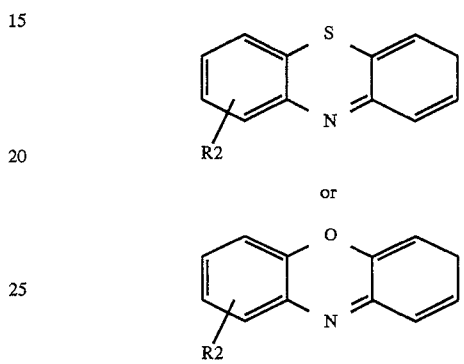

with a R1 substituted or unsubstituted aromatic amine in the presence of periodic acid in a polar organic solvent capable of dissolving the reactants for a time sufficient to form the desired product.

DESCRIPTION OF THE INVENTION

The present invention involves an improved method for the preparation of substituted or unsubstituted 3-phenylimino-3H-phenothiazines and phenoxazines. These compounds have been found to be particularly useful as mediators for the oxidation of NADH, NADPH or analogs thereof on an electrode. Studies have shown water solubility and stability at basic pH are necessary in order to prepare a monomeric mediator which performs well with reductive enzymes. Substitution on the phenyl ring provides a handle for the solubility and stability of this class of compounds. Unfortunately, there are only a few literature methods for the preparation of the substituted 3-phenylimino compounds and, in general, the products isolated are poorly characterized and obtained in low yields with extensive purification being required.

The 3-phenylimino compounds are typically prepared by the oxidation of phenothiazine or phenoxazine by bromine or iodine. The subsequent treatment by an amine yields a mixture of the 3 and the 3,7-bis(substituted amino)-phenothiazin-5-ium salt. This was demonstrated by Shinezi et al. in *J. Heterocyclic Chem.*, 30, 1693 (1993). Baranov et al., Zhurnal Organicheskoi Khimii, Vol. 27, No. 9, Pp. 2008–2014 (1989) encountered similar mixed products by reacting aromatic amines in the presence of oxidizing agents containing ferric ions.

It has now been discovered that periodic acid ($H_5IO_6$) is a preferred coupling agent in this preparation in terms of the yield and purity of the recovered product. While it is not intended to be limited by any particular mechanism of reaction for the synthesis of the present invention, it is believed that the periodic acid is superior to other oxidative coupling reagents because experiments have shown that the 3,7-bis(substituted amino)phenothiazine is not normally formed even when using reactant ratios and reaction conditions which give almost exclusively the bis substituted products by other methods. Because the reaction gives only the mono-substituted product, and because the ratio of the aromatic amine to phenothiazine or phenoxazine is 1 to 1, there are no excess reagents to remove and fewer possible side reactions thereby providing a product having significantly greater purity than is obtainable by using prior art methods.

While the ratio of reactants to the periodic acid coupling agent is not critical for reaction, it is preferred that the molar ratio of phenothiazine or phenoxazine to aromatic amine be close to 1:1 with the molar concentration of periodic acid being such that it is present in a ratio of from about 4 to 6 equivalents with regard to the reactants. Four or more equivalents of periodic acid give the best results because side reactions occur if the reaction proceeds too slowly. When iodine or ferric chloride are used as the oxidative coupler there is typically employed a molar excess of aromatic amine to phenothiazine or phenoxazine on the order of 1.2 to 2 equivalents of amine to 1 of the phenothiazine or phenoxazine. The excess amine causes the reaction to proceed more rapidly by making it basic. In addition it is easier to remove excess amine, as opposed to phenothiazine or phenoxazine on a column. Since these reactions can form the bis-substituted product, some excess is necessary to maximize the yield of desired product. The use of periodic acid facilitates the use of a 1:1 ratio of the other reagents thereby eliminating the formation of side products which are inherent in these techniques. Other advantages inherent in the method of the present invention are high yields of the desired product and the capability of recovering it by simple filtration from its reaction medium. Reaction temperature is not critical (typically at ambient temperature) under ambient pressure conditions. The reaction may be cooled to 0° C. to minimize the risk of side reactions and to maximize yield.

The reaction is carried out in a polar organic solvent capable of dissolving the reactants. Suitable solvents include methanol, ethanol, acetone and tetrahydrofuran. Since the reaction product is insoluble or may be precipitated in the solvent system in which the coupling reaction is carried out, it can be recovered by simple filtration using, for example, a Buchner funnel or filter paper as the filtration means. While the desired product is recovered in good purity, it can be further purified by filtration through silica gel using $CH_3Cl_3/EtOH$ if desired.

It is evident that R1 and R2 in the foregoing formulae can represent a variety of substituent groups without departing from the scope of the present invention. Such substituent groups are limited only by the ability of one of ordinary skill in the art to prepare stable compounds under the reaction conditions. For example, in the above formulae, substituents R1 and R2 may be the same or different and may represent a single or multiple substituents. These substituents may be selected from, but are not limited to hydrogen, alkyl of 1 to 20 carbon atoms, aryl, halo, haloalkyl, carboxy, carboxyalkyl, alkoxycarbonyl, aromatic or aliphatic keto, alkoxy, aryloxy, nitro, dialkylamino, aminoalkyl, sulfo, dihydroxyboron (—$B(OH)_2$) and the like. It is also contemplated that aliphatic and aromatic groups incorporated into R1 and R2 can themselves bear a variety of substituent groups.

When the phenothiazines and phenoxazines prepared by the process of the present invention are to be used as mediators, R1 and R2 may be selected from those moieties which serve to modulate the reduction-oxidation potential of the mediator, to vary the compounds solubility or to function as a handle for covalent attachment of the mediator to a polymer or solid support.

The phenothiazines and phenoxazines of the present invention can be represented by a single formula in which the symbol X is used to represent sulfur and oxygen.

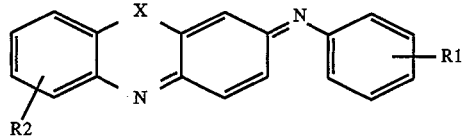

The method of practicing the present invention is further illustrated by the following examples:

EXAMPLE I (General Example)

Phenothiazine (5 mMol) and an aromatic amine (5 mMol) are dissolved together in 150 ml of methanol at ambient temperature. Periodic acid (30 mMol) is dissolved in 40 ml of water and added in one portion to the stirring phenothiazine solution. The mixture is stirred for 20 minutes and the solid collected on a filter, washed with 100 ml of saturated sodium thiosulfate and 200 ml water and dried to provide pure product in high (85%) yield.

EXAMPLE II

Preparation of 3-(4-methoxyphenylamino)-3H-phenothiazine.

Phenothiazine, 0.5 g/0.0025M, and p-anisidine, 0.307 g/0.0025M, were dissolved in 50 ml of methanol and stirred at ambient temperature. Periodic acid, 3.4 g/0.015M, was dissolved in 40 ml of methanol and the solution added in one portion to the stirring phenothiazine mixture. The reaction mixture was stirred for 20 minutes and then poured into 100 ml of water with solid residue being collected by a Buchner funnel. The solid was stirred with 200 ml of a 1:1 mixture of $MeOH/H_2O$ and collected. The red-brown solid was dried to yield 0.72 g (91% theory) of the desired product having a melting point of 135°–136° C. (lit. 148°–149° C.).

| Elemental analysis | Theoretical | Found |
| --- | --- | --- |
| C | 71.67 | 71.23 |
| H | 4.43 | 4.38 |
| N | 8.80 | 8.56 |

Mass spectral, carbon and proton NMR analysis were consistent with the structure of the desired product. The yield reported in the literature, i.e. U.S. Pat. No. 4,710,570 using $I_2$ was 71%. The yield reported by Baranov et al using $FeCl_3$ was 67%.

EXAMPLE III

Preparation of 3-(4-trtfluoromethylphenylimino)-3H-phenothiazine.

Phenothiazine, 1.0 g/0.005M, and 4-aminobenzotrifluoride, 0.8 g/0.005M, were dissolved in 150 ml of methanol and stirred at ambient temperature. Periodic acid, 6.8 g/0.030M, was dissolved in 40 ml of water and added in one portion to the stirring phenothiazine mixture. The reaction was stirred for 20 minutes and the solid collected on a Buchner funnel. The solid was washed with 200 ml of water and 200 ml of methanol/water. The red-brown solid was dried to yield 1.81 g (100% of theory) of product having a melting point of 204°–205° C.

| Elemental Analysis | Theoretical | Found |
|---|---|---|
| C | 62.45 | 62.59 |
| H | 3.3 | 3.19 |
| N | 7.67 | 7.62 |

Mass spectral, carbon and proton NMR analysis were consistent with the structure of the desired product.

EXAMPLE IV

Preparation of 3-(3,5-dinitrophenylamino)-3H-phenothiazine.

Phenothiazine, 1.0 g/0.005M) and 3,5 dinitroanaline, 0.92 g/0.005M) were dissolved in 150 ml of MeOH and stirred at ambient temperature. Periodic acid 6.8 g/0.030M, was dissolved in 40 ml of water and added in one portion to the stirring phenothiazine mixture. The reaction stirred for 20 minutes whereupon the solid was collected on a Buchner funnel and washed with 200 ml of saturated sodium thiosulfate solution and 200 ml of water. The product was dissolved in 9:1 $CHCl_3$/EtOH and filtered through silica gel. The solvent was removed in vacuo and the solid dried to yield 1.1 g (67% theory) of a red-brown solid having a melting point of 253°–255° C.

| Elemental Analysis | Theoretical | Found |
|---|---|---|
| C | 55.88 | 56.33 |
| H | 2.86 | 2.83 |
| N | 14.46 | 14.39 |

Mass spectral, carbon and proton NMR analysis were consistent with the structure of the desired product.

The yield of this product was lower than that of the previous two examples. However, this compound was not isolated when iodine was used as the coupling agent. This compound is not mentioned in the literature.

EXAMPLE V

Preparation of 3-(4-nitrophenyl)imino-3H-phenothiazine.

Phenothiazine, 0.5 g/0.0025M, and 4-nitroanaline, 0.345 g/0.0025M, were dissolved in 50 ml of methanol and cooled to 0°–5° C. with stirring. Periodic acid, 3.4 g/0.015M, was dissolved in 40 ml of methanol and the resulting solution added in one portion to the stirring phenothiazine mixture. After 20 minutes, 45 ml of water was added and the mixture stirred for 5 minutes. The solid product was collected using a Buchner funnel and washed with 250 ml of a 1:1 mixture of methanol/water. The solid was dried to yield 0.71 g (85%) of a brown-red solid having a melting point of 203°–204° C. (reported 207°–208° C.).

| Elemental Analysis | Theoretical | Found |
|---|---|---|
| C | 63.1 | 62.86 |
| H | 3.53 | 3.44 |
| N | 12.27 | 11.95 |

Mass spectral, carbon and proton NMR analysis were consistent with the structure of the desired product.

The subject compound was prepared in 5% yield after 2 purifications by chromatography using iodine and in 9% yield using ferric chloride as reported by Baranov et al.

What is claimed is:

1. A method for the preparation of substituted 3-(phenylimino)-3H-phenothiazine or phenoxizine characterized by the formula:

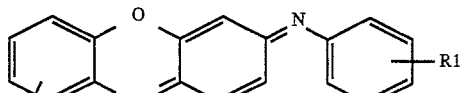

or

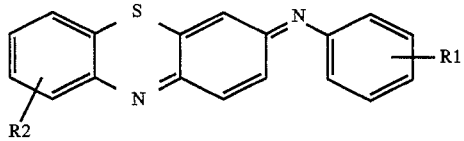

wherein R1 and R2 are H or one or more substituents which serve to modulate the reduction-oxidation potential of the compound, to vary the compound's solubility or to function as a site for the covalent attachment of the compound to a polymer or solid support which method comprises reacting a phenothiazine or phenoxazine of the formula:

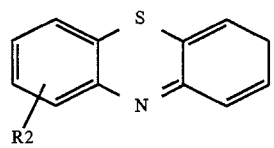

or

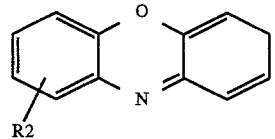

with a R1 substituted or unsubstituted aromatic amine in the presence of periodic acid in a polar organic solvent capable of dissolving the reactants for a time sufficient to form the desired product.

2. The method of claim 1 wherein a phenothiazine is reacted with the aromatic amine to form a 3-(phenylamino)-3H-phenothiazine.

3. The method of claim 1 wherein a phenoxizine is reacted with the aromatic amine to form a 3-(phenylamino)-3H phenoxizine.

4. The method of claim 1 wherein the ratio of the aromatic amine to phenothiazine or phenoxazine is approximately 1:1.

5. The method of claim 1 wherein the periodic acid is present in a ratio of from about 4 to 6 equivalents with regard to the reactants.

6. The method of claim 1 wherein the aromatic amine is aniline.

7. The method of claim 1 wherein R1 and R2 are hydrogen, alkyl, aryl, halo, haloalkyl, carboxy, carboxyalkyl, alkoxycarbonyl, aromatic or aliphatic keto, alkoxy, aryloxy, nitro, dialkylamino, aminoalkyl, sulfo or dihydroxyboron (—$B(OH)_2$).

8. The method of claim 1 wherein R1 is 4-methoxy.

9. The method of claim 1 wherein R1 is 3,5-dinitrophenylamino.

10. The method of claim 1 wherein R1 is 4-nitrophenyl.

* * * * *